(12) United States Patent
Kohichi et al.

(10) Patent No.: US 6,646,185 B2
(45) Date of Patent: Nov. 11, 2003

(54) GENETIC TRANSFORMATION METHOD FOR ZOYSIAGRASS

(75) Inventors: Tohyama Kohichi, Sunchon (KR); Chang-Hyu Bae, Sunchon (KR); Jeong-Gu Kang, Kwangju (KR); Pill-Soon Song, Kwangju (KR); Chung-Mo Park, Kwangju (KR); Hyo Yeon Lee, Sunchon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/988,580

(22) Filed: Nov. 20, 2001

(65) Prior Publication Data

US 2003/0106108 A1 Jun. 5, 2003

(51) Int. Cl.7 .................. C12N 15/82; C12N 15/74; A01H 5/00; C07H 21/04
(52) U.S. Cl. .................. 800/294; 435/244; 435/320.1; 435/419; 435/430; 435/431; 536/23.1; 800/295; 800/278; 800/300; 800/320
(58) Field of Search .............. 536/23.1; 435/320.1, 435/419, 430, 431, 244; 800/295, 278, 294, 300, 320

(56) References Cited

PUBLICATIONS

Rathus, C, et al, Effects of paromoter, intron & enhancer elements on transient gene expression in sugar–cane & carrot prototplasts; Plant Molecular biology, 23: 613–618, 1993.*

Van der Leede–Plegt, LM, et al, Introduction & differential use of various promoters in pollen grains of *Nicotiana glutinosa* & *Lilium longiflorum*.; Plant Cell Reports 11: 20–24., 1992.*

Keith B, et al, Monocot and dicot pre–mRNAs are processed with different efficiencies in transgenic tobacco; EMBO Journal 5: 2419–2425, 1996.*

Ke et al, Plant Cell Reports (1996) 15, pp. 882–887, "Plant regenteration in Kentucky bluegrass (*Poa pratensis* L) . . . ".

Inokuma et al, Plant Cell Reports (1998) 17, pp. 334–338, "Transgenic Japanese lawngrass (*Zoysia japonica* Steud) . . . ".

Asano, Plant Cell Reports (1989) 8, pp. 141–143, "Somatic embryogenesis and protoplast culture in Japanese . . . ".

Chai et al, Crop Sci. 38(1998), pp. 1320–1338, Applications of Biotechnology in Turfgrass Genetic Improvement.

Hiei et al, The Plant Journal 6(2), (1994), pp. 272–282, "Efficient transformation of rice (*Oryza sativa* L.) . . . ".

Dong et al, Molecular Breeding 2, (1996), pp. 267–276, "Agrobacterium–mediated transformation of Javanica rice".

Cheng et al, Physiol. (1997) 115, pp. 971–980, Genetic Transformation of Wheat Mediated by *Agrobacterium tumefaciens*.

* cited by examiner

Primary Examiner—Phuong T. Bui
Assistant Examiner—Georgia Helmer
(74) Attorney, Agent, or Firm—Jacobson Holman PLLC

(57) ABSTRACT

The present invention provides an efficient genetic transformation system for the zoysiagrass plant (*Zoysia japonica* Steud.). Also provided are optimized media compositions and culture conditions for the zoysiagrass transformation. The reliable transformation system for zoysiagrass was developed by optimizing several factors that significantly affect calli growth and plant regeneration. Callus type and co-cultivation period absolutely influenced the transformation efficiency. Concentrations of 2,4-D, $CaCl_2$ and acetosyringone were also critical factors. The best result was achieved when type 3 calli were co-cultivated on a 2,4-D-free co-cultivation medium for 6 days. Removal of calcium and addition of 50 mg/liter acetosyringone during co-cultivation drastically enhanced the efficiency. The invention also provides a bialaphos-resistant zoysiagrass plant, which can be used in golf courses and athletic fields to save the maintenance cost.

3 Claims, 7 Drawing Sheets

GENETIC TRANSFORMATION METHOD FOR ZOYSIAGRASS

BACKGROUND OF THE INVENTION

This invention relates to an efficient genetic transformation method for zoysiagrass (*Zoysia japonica* Steud.), also called Korean grass. The present invention can be applicable to other closely related turfgrass species. The present invention also provides the transgenic zoysiagrass plant that is resistant to herbicide and the experimental methods and processes for the generation of such a herbicide-resistant zoysiagrass.

The present invention is to provide an efficient *Agrobacterium tumefaciens*-mediated genetic transformation method for zoysiagrass (*Zoysia japonica* Steud.), also known as Korean grass, the optimised media composition and culture condition that greatly influence the transformation efficiency, and the transgenic zoysiagrass plant that has herbicide resistance and associated experimental procedures for the development of such a transgenic zoysiagrass with the bialaphos resistance gene (bar).

Zoysiagrass is one of the most important species of turfgrass and widely cultivated in the Far-Eastern Asia, including Korea, Japan, and Eastern area of China, as well as in the temperate zone worldwide. The cultivation area of zoysiagrass is rapidly expanding in USA and other countries in recent years, primarily due to its extraordinary characteristics such as the resistance to drought and the capacity to rapidly recover from traffic damage. In addition, it grows well in poor soil in virtually all climates. Due to these useful traits, it is widely used for golf courses, athletic fields, roadsides, home gardens, and riverbanks. As its market size is rapidly growing, customers demand new varieties with improved resistance to pathogens, herbicides, and various environmental stresses. Until recently, classical breeding methods have been mainly employed to develop such new traits in turfgrass. However more and more laboratories and institutes are striving to apply molecular biological methods to genetically engineer turfgrass (Inokuma et al. 1998; Park and Ahn 1998) since it is now possible to develop or modify useful traits in a predictable way by using these methods.

Although most monocots are not readily infected by *Agrobacterium tumefaciens*, efficient *A. tumefaciens*-mediated transformation systems have been successfully recently developed for a few species of the Gramineae family, such as rice (Hiei et al. 1994; Rashid et al. 1996), maize (Ishida et al. 1996), and wheat (Cheng et al. 1997). Unfortunately, however, such *A. tumefaciens*-mediated transformation methods have not been established yet for turfgrass (Chai and Sticklen 1998) except for the bentgrass (Yu et al. 2000). Especially, the genetic transformation of zoysiagrass is further hampered by some additional technical problems. For example turfgrass seed germination rate is very low, and production of regenerable callus is difficult (Asano 1989).

Callus morphology is closely related to plant regenerability as has been proven in various plant species (Armstrong and Green 1985; Ke and Lee 1996; Luo and Jia 1998). Recently, we established an efficient callus induction and plant regeneration system for zoysiagrass (Bae et al. 2001), which was filed as U.S. Pat. Ser. No. 09/915,294 on Jul. 27, 2001.

According to the present invention, it is now possible to genetically transform zoysiagrass with a gene of interest by *A. tumefaciens*-mediated infection.

Some potential target traits for the genetic transformation of zoysiagrass include improved ground-covering capacity, tolerance to traffic injury, rapid recovering after damage, resistance to biotic and abiotic stress, engineered (accelerated or delayed) growth rate, and shade avoidance. Of particular interests is to engineer growth rate and/or shade avoidance so that the maintenance cost for watering and mowing can be drastically reduced.

With recent rapid accumulation of molecular biological technology and establishment of efficient tissue culture and genetic transformation systems in plants, any gene of agronomical importance can now be readily introduced into any desired plants with aims to enhance crop yield and quality and environmental adaptability. In the present invention, we provide an efficient *Agrobacterium tumefaciens*-mediated zoysiagrass transformation method and a transgenic zoysiagrass plant with herbicide resistance.

As used herein, the term "genetic transformation" refers to a procedure to introduce a gene(s) or genetic material(s) into a higher plant of interest in a predictable way. The gene or genetic material is stably integrated into the plant genome and transmitted through generations.

SUMMARY OF THE INVENTION

The present invention relates to a reliable *Agrobacterium tumefaciens*-mediated transformation method for zoysiagrass that is to be routinely used for the genetic transformation of zoysiagrass or closely related turfgrass species.

The present invention also provides a method for genetically transforming the zoysiagrass (Zoysia genus) comprising the steps of: i) inducing and growing the calli of zoysiagrass on modified MS medium containing various hormones; ii) infecting the calli of zoysiagrass with Agrobacterium cells to introduce bialaphos resistance bar gene; iii) co-cultivating calli of zoysiagrass and Agrobacterium cells in co-cultivation medium containing acetosyringone without 2,4-dichlorophenoxyacetic acid and calcium; iv) eliminating Agrobacterium cells from co-cultivation medium; and v) regenerating the transgenic zoysiagrass.

Further, Agrobacterium cells possess the pGPT-HB transforming vector, and type 3 calli (which is defined in our previous application Ser. No. 09/915,294) are co-cultivated in co-cultivation medium for 5~7 days.

Also, the present invention provides a transgenic zoysiagrass by above method, which is stably transformed with the bar gene under control of plant-specific promoter. The particular promoter is ubiquitin promoter from maize.

Critical media components or culture conditions evaluated in the invention include callus type, co-cultivation period, 2,4-D (2,4-dichlorophenoxyacetic acid), $CaCl_2$, and acetosyringone. The highest transformation efficiency was obtained when type 3 callus was co-cultivated on a 2,4-D-free medium for 5~7 days. In addition, removal of calcium and inclusion of 30~70 mg/liter acetosyringone during co-cultivation greatly enhanced the transformation efficiency.

When the optimized transformation protocol was used for zoysiagrass transformation with the bar gene, up to 20.5% of plated shoots on the selection medium exhibited herbicide-resistant.

Also, provided in the invention is the transgenic zoysiagrass plant with herbicide resistance. The transgenic zoysiagrass could survive even after 5 gram/liter herbiace solution was sprayed every day for 2 weeks and eventually grew to maturity, whereas control plants stopped growing and died when treated under the same experimental condition.

Therefore, the present invention further provides the transgenic zoysiagrass callus with herbicide resistance (deposited under accession No. KCTC-10076BP).

Said callus was deposited at Korea Collection for Type Cultures, #52 Oun-Dong, Yusong-ku, Taejon, Seoul, 305-333, Republic of Korea with accession number KCTC-10076BP on Sep. 21, 2001 under Budapest treaty.

BRIEF DESCRIPTION OF THE DRAWINGS

FIG. 1A shows Type 1 calli have whitish-yellow or pale-green color and show a compact and non-friable structure.

FIG. 1B shows Type 2 calli are white and show a compact and friable structure.

FIG. 1C shows Type 3 calli are yellow and show a compact and very friable structure.

FIG. 1D shows Type 4 calli are translucent with a soft and watery appearance. The four callus types were obtained on the callus growth media supplemented with different combinations of growth regulators as summarized in Table 2.

FIG. 6A shows plants were not sprayed with herbicide solution.

FIG. 6B shows plants were daily sprayed with herbicide solution for 2 weeks.

FIG. 7A shows vector map of the transformation vector pGPTV-HB. Phons, promoter of nopaline synthase gene; $Hyg^R$, hygromycin-resistance gene (HPT); NOS, terminator of nopaline synthase gene; Ubi-P, ubiquitin promoter from maize; Bar, bialaphose-resistance gene; B, BamHI; E, EcoRI; H, HindIII; S, SacI.

FIGS. 7B and 7C shows southern blot analyses of a transgenic zoysiagrass plant. Genomic DNAs were digested either with HindIII (lane 1) or with Bam HI (lane 2). Membranes were hybridized either with the bar FIG. 7B or the hpt FIG. 7C probe. Genomic DNA of an untransformed plant was included as a negative control (lane c).

DETAILED DESCRIPTION OF THE INVENTION

Figure 1:
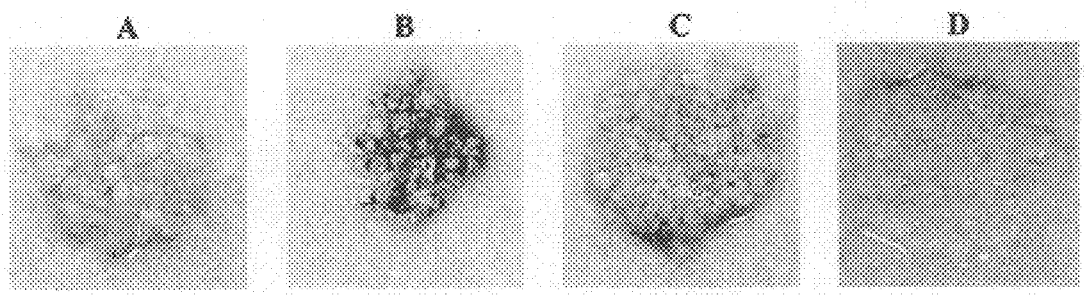
FIG. 1 shows four different types of calli grown on the callus growth medium.

Genetic transformation of agronomically important plants is a potential way to develop new varieties of a plant species with novel or improved useful traits. The target traits relevant to crop plants include improved or delayed growth rate, enhanced resistance to biotic and abiotic stress, increased yield, and flexible adaptability to environmental fluctuations. The prerequisite for successful plant genetic transformations is a reliable system for tissue culture and plant regeneration and a consistent delivery device of genetic materials. With recent advances in plant molecular biology and methodologies, any gene of interest can be easily delivered to any plant species of interest. However some crop plants, especially monocots, are reluctant to genetic manipulation, and it is not easy to carry out plant regeneration in ordinary laboratories. Turfgrass is widely used for diverse purposes, including golf courses, lawn grounds, home gardens, and recreation parks and is emerging as a potential commercial target plant for plant biotechnological applications in recent years. However, no efficient tissue culture and genetic transformation systems have been developed. As a result, biotechnological genetic manipulation of turfgrass was not far advanced yet.

The present invention provides the optimised media compositions and culture conditions for efficient genetic transformation and plant regeneration from seed-derived calli of zoysiagrass. The zoysiagrass, a subtype of the warm season turfgrass, is widely distributed and cultivated in the temperate zone, including Far-Eastern Asia. Furthermore, the cultivating area is rapidly expanding in recent years due to several advantages, such as resistance to drought and traffic damage. In this invention, the most efficient transformation was achieved when type 3 calli were co-cultivated on a co-cultivation medium that is free of 2,4-D but with 50 mg/liter acetosyringone for 6 days. Calcium, that is known to improve the transformation efficiency in other plants, has a negative effect. Plant tissue culture and regeneration experiments are routinely performed in well-established plant molecular laboratories and well known to the art in this field.

The present invention also relates to a herbicide-resistant zoysiagrass plant that can survive even after sprays of bialaphos solution every day for 2 weeks. By growing this transgenic zoysiagrass in golf courses and athletic fields, it will be easier to selectively remove weeds just by spraying herbicides, and the maintenance cost will drastically decrease. In addition, less amount of fertilizers is expected to be required to grow the transgenic zoysiagrass since the nutrition-consuming weeds are efficiently removed. The transgenic zoysiagrass did not show any morphological distortions and grew well, indistinguishable from the parental plants.

The present invention also can be applied to other closely related turfgrass species as well as possibly of other monocot species that belong to the Gramineae family. Experimental procedures for the development of such genetically engineered plants are well known to the art. This is the first invention for the efficient A. tumefaciens-mediated transformation of zoysiagrass by using highly regenerable callus line.

EXAMPLES

Preparation of Regenerable Calli

Approximately one hundred mature seeds of zoysiagrass (*Zoysia japonica* Steud.) were surface-sterilized with 1 ml of 2% sodium hypochlorite for 15 mm in 2-mil centrifuge tube with agitation using a tube mixer. The seeds were then washed three times with sterilized double-distilled water. For callus induction, approximately 100 seeds were plated on filter paper-laid MS (Murashige and Skoog 1962) medium petridish containing 3% sucrose (w/v), 100 mg/liter α-ketoglutaric acid, 4 mg/liter thiamine-HCl, 2 mg/liter 2,4-D, 0.2 mg/liter BA, and 0.2% Gelrite™(w/v). The medium was adjusted to pH5.8 using HCl before autoclaving at 1.2–1.3 kg/cm$^2$ pressure and 121° C. for 20 min. Callus induction was performed in a culture room at 26±1° C. in complete darkness for three months. Each petridish (90 mm in diameter) contained about 30 ml of media an was tightly sealed with parafilm (American National Can, USA). After additional three-day incubation under continuous white light with an intensity of 30 μmol m$^{-2}$s$^{-1}$ provided by fluorescent tubes, only green tissues were transferred to MS media containing 1 mg/liter 2,4-D and 0.2 mg/liter BA and subsequently cultured in the dark for further growth. After 5 weeks of culture in the dark, independent seed-derived calli with green color were transferred and further cultured on filter paper-laid MS media containing different hormonal combinations of 2,4-D and BA in the dark. Four types of calli were finally obtained. Type 1, 2 and 4 calli were generated on the 1 mg/liter 2,4-D-containing media, and type 3 calli on the 4 mg/liter 2,4-D-containing media after subculturing at four-week intervals (FIG. 1). Each petridish (90 mm in diameter) contained 25 ml media and was sealed with Micropore Surgical Tape (3M Health Care, USA).

Characterization of Four Callus Types

To investigate morphological changes occurring on type 1 calli subculturing, type 1 calli were transferred to a MS medium containing various hormonal combinations of 2,4-D (1, 2, 4, and 8 mg/liter) and BA (0, 0.01, and 0.1 mg/liter) in the dark. After five weeks of subculturing in the dark, four callus types were observed. Each callus type was weighed, and the weight ratios were calculated. Calli of types 2, 3, and 4 were also examined in an identical way as with type 1 callus.

Optimized Conditions for Agrobacterium-Infection

An *A. tumefaciens* disarmed strain EHA101 containing pIG121Hm was used for this experiment. The T-DNA of pIG121Hm contained a hygromycin-resistant gene (hpt), a kanamycin-resistant gene (npt), and an intron-gus gene (uidA). *Agrobacterium tumefaciens* cells were grown at 28° C. overnight with shaking at 160 rpm in 100 ml Erlenmeyer flask containing 20 ml LB medium (Table 1) supplemented with 50 mg/liter hygromycin, 100 mg/liter kanamycin, and 100 mg/liter spectinomycin (pGPTV-HB).

Table 1 shows different media and their compositions used in the zoysiagrass transformation system.

TABLE 1

Media used in the zoysiagrass transformation procedure

| | |
|---|---|
| Callus induction | MS salts and modified vitamins (4 mg/l thiamine-HCl), 30 g/l sucrose, 2 mg/l 2,4-D, 0.2 mg/l BA, 2 g/l Gelrite ™, pH 5.8 (MSCI) |
| Callus growth (MSCG1) | MS salts and vitamins, 30 g/l sucrose, 1 mg/l 2,4-D, 0.01 mg/l BA, 2 g/l Gelrite ™, pH 5.8 |
| Callus growth (MSCG2) | MSCG1 plus 4 mg/l 2,4-D |
| Agrobacterium culture (LB) | 1% tryptone, 5 g/l yeast extract, 5 g/l NaCl, spectinomycin (for only pGPTV-HB), pH 7.0 |
| Agrobacterium resuspension (LqMSAS) | Calcium-free MS salts and vitamins, 30 g/l sucrose, 10 g/l glucose, 100 mg/l betaine, 50 mg/l acetosyringone, 0.01% pluronic F68, pH 5.2 |
| Co-culture (MSAS) | LqMSAS plus 0.01 mg/l BA, 2 g/l Gelrite ™ and 0.01% pluronic F68 |
| Callus growth and agrobacterium elimination (MSCGCB) | MSCG1 plus 500 mg/l calbenicillin |
| Shoot induction (MSSI) | MS salts and vitamins, 30 g/l maltose, 1 mg/l BA, 2 g/l Gelrite ™, 250 mg/l carbenicillin, pH 5.8 |
| Root induction and selection (MSRS) | MS salts and vitamins, 30 g/l sucrose, 1 mg/l GA$_3$, 2 g/l Gelrite ™, 250 mg/l carbenicillin, 5 mg/l bialaphos or 10 mg/l hygromycin, pH 5.8 |
| Plant growth (MSPG) | MS salts and vitamins, 30 g/l sucrose, 8 g/l agar, pH 5.8 |

Cells in 10 ml of the suspension culture were collected in a 50 ml polypropylene tube (Becton Dickinson Labware, USA) by centrifugation at 2500 rpm for 20 min and resuspended in 10 ml liquid infection medium (LqMSAS in Table 1) by gentle vortexing.

Acetosyringone was prepared by dissolving an appropriate amount of powder in dimethyl sulfoxide at a concentration of 100 mg/ml and stored at 4° C. in the dark. It was added to the sterile medium to an appropriate final concentration whenever required. The calli proliferated on the MSCG4 medium were immersed in the Agrobacterial cell suspension for 1 min. After dehydration on sterile filter paper, the calli were cultivated on a co-cultivation medium (MSAS) with 4 mg/liter 2,4-D at 26±1° C. in the dark for 15 days. After co-cultivation, the calli were thoroughly washed by vortexing in sterile double-distilled water supplemented with a surfactant (0.02% pluronic F68) until the washing solution becomes transparent and finally washed in sterile double-distilled water containing 1000 mg/liter calbenicillin and 0.02% surfactant. After washing, an half of the calli were used for GUS activity assay by the method described by Schenk et al. (1998).

Several factors were tested to optimize transformation efficiency. (1) For comparison of different callus types on invasiveness, types 1, 2 and 3 calli were co-cultivated on 2,4-D-free MSAS media for 6 days; (2) For comparison of co-cultivation periods, calli were co-cultivated for 3, 6, 9, 12, 15, 18, 21, 24 and 27 days; (3) For examination of media components, different amounts of 2,4-D (0, 1, 2, 4, and 8 mg/liter), CaCl$_2$ (0, 11, 110, 220, and 440 mg/liter), and acetosyringone (0, 10, 50, 100, and 200 mg/liter) were added to the MSAS media.

pGPTV-HB Co-cultivation

The optimized conditions for the *A. tumefaciens* infection of zoysiagrass calli included the use of type 3 calli as donor, a co-cultivation period of 9 days, the exclusion of 2,4-D and CaCl$_2$ from the media, and the use of 100 mg/l acetosyringone. All the media and their compositions used for the experiments are summarized in Table 1. After pGPTV-HB co-cultivation, calli were transferred to filter paper-laid MSCG media and cultured for 2–4 weeks in the dark. The calli were then transferred to filter paper-laid MSSI medium for shoot induction. Various concentrations (125, 250, and 500 mg/liter) of calbenicillin were added to the shoot induction medium. Induced shoots were subsequently transferred to the MSRS medium for rooting and selection for 4 weeks. Five mg/liter bialaphos and 10 mg/liter hygromycin were used for selection of bialaphos- and hygromycin-resistant plantlets. The rooting plants on the selection medium were transferred to the MSPG medium without antibiotics and bialaphos and further grown. The fully grown plants were then transferred to a pot containing soil and grown in an environmentally controlled growth chamber set at 30° C., 80% relative humidity and 18-hour photoperiod with 30 $\mu$molm$^{-2}$s$^{-1}$ irradiance provided by cool white fluorescent tubes. When the roots developed enough, pots were transferred to green house.

Analysis of Transgenic Zoysiagrass Plant

The putative transgenic zoysiagrass plants were sprayed with 5 gram/liter herbiace solution (1 gram/liter bialaphos, Meiji Seika, Japan) in order to examine whether they were resistant to herbicide. In addition, to investigate whether the herbicide resistant gene is incorporated into the plant genome, genomic DNA was isolated from the leaves of the transgenic plants by following the method of Roger and Bendich (1985). Twenty $\mu$g of HindIII- or BamHI-digested genomic DNA was separated on a 0.8% agarose gel, blotted onto a nylon membrane (Hybond-N$^+$) by standard methods (Southern 1975), and probed with a $^{32}$P-labeled hpt gene sequence or bar gene sequence. The probes were prepared by random priming (Sambrook et al. 1989).

Results

Callus Morphology Suitable for Agrobacterial Infection

Culture of the mature seed-derived type 1 calli on a MS medium containing various combinations of 2,4-D and BA resulted in a mixture of callus types 1–4 (Table 2).

Table 2 shows differential growths of zoysiagrass type 1 calli on media containing different combinations of growth regulators. Ten mg of type 1 calli was grown on MS media with various combinations of 2,4-D and BA and 2 g/liter Gelrite™ for 5 weeks in the dark at 28° C. Each value represents a mean calculated from ten calli. Callus morphologies were rated by; 1=whitish-yellow, compact and non-friable, 2=white, compact and friable, 3=yellow, compact and very friable, 4=translucent, soft and watery.

TABLE 2

Effects of different combinations of growth hormones on type 1 callus growth

| GRC (mg/l) | | Callus fresh weight (mg ± SE) | | | | | Mixture rate |
|---|---|---|---|---|---|---|---|
| 2,4-D | BA | Total | Type 1 | Type 2 | Type 3 | Type 4 | (type 1:2:3:4) |
| 1 | 0 | 8.5±9.1 | 45.8±16.3 | 22.3±5.2 | 0 | 13.4±2.7 | 56:27:0:16 |
| 1 | 0.01 | 115.7±11.8 | 67.4±9.1 | 32.3±5.2 | 6.1±3.7 | 9.9±3.2 | 58:28:5:9 |
| 1 | 0.1 | 68.0±8.3 | 36.0±15.5 | 10.3±4.3 | 2.9±2.2 | 18.8±3.1 | 53:15:4:28 |
| 2 | 0 | 37.0±11.3 | 18.8±12.5 | 2.3±0.9 | 1.5±1.5 | 14.5±3.7 | 51:6:4:39 |
| 2 | 0.01 | 85.2±19.3 | 31.9±10.8 | 9.5±2.9 | 27.2±12.3 | 16.6±4.1 | 37:11:32:19 |
| 2 | 0.1 | 43.7±9.0 | 10.9±4.9 | 2.7±1.5 | 12.8±5.0 | 17.3±3.0 | 25:6:27:40 |
| 4 | 0 | 29.6±4.2 | 11.4±3.4 | 0 | 0.9±0.9 | 17.2±3.2 | 39:0:3:58 |
| 4 | 0.01 | 57.0±9.6 | 13.4±4.3 | 0 | 33.7±11.3 | 9.9±2.6 | 24:0:59:17 |
| 4 | 0.1 | 38.4±13.1 | 18.0±6.0 | 7.4±5.6 | 7.7±3.4 | 5.3±2.1 | 47:19:20:14 |
| 8 | 0.01 | 17.8±6.5 | 2.1±1.1 | 0 | 5.5±5.3 | 10.1±3.0 | 12:0:31:57 |

Figure 2:
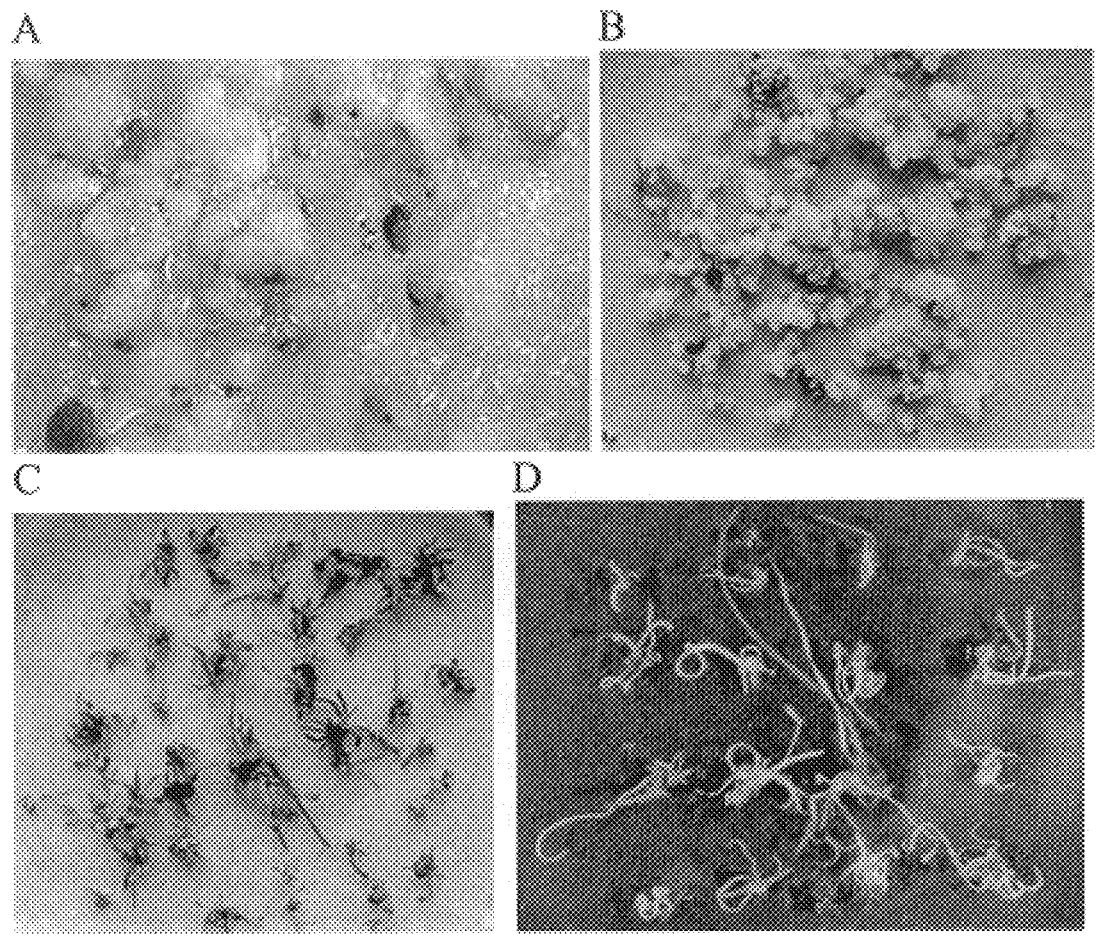
FIG. 2 shows transgenic GUS expressions in zoysiagrass calli infected with A. tumefaciens harbouring the pGPTV-HB vector (see FIG. 7). (A) Transgenic GUS expression in zoysiagrass calli. (B) Rapid growth of the calli on a filter paper-laid and antibiotics-free MSCGCB medium after A. tumefaciens infection. (C) Shoot induction on a filter paper-laid and antibiotics-free shoot induction media. (D) Shoot elongation and rooting on a bialaphos-containing medium. Shoots induced from the A. tumefaciens-infected calli were cultured on a selective rooting medium MSRS containing 5 mg/liter bialaphos.

The resultant four types of calli were morphologically characterized. Type 1 calli were whitish-yellow or pale green with a compact and non-friable structure. Multiple shoot primordia were observed on the surface of some type 1 calli (FIG. 1A). Type 2 calli were white with a compact and friable structure (FIG. 1B). Type 3 calli were yellow and had a compact and very friable structure (FIG. 1C). Type 4 calli were unique in that they were translucent with a soft watery appearance (FIG. 1D). Types 1–3 calli were regenerable, whereas type 4 calli were not. The best propagation and incidence rate of types 1 and 2 calli (67.4±9.1 mg, 58% and 32.3±5.2 mg, 28%, respectively) and type 3 calli (33.7±11.3 mg, 59%) were obtained on a MS medium containing 0.01 mg/liter BA in a combination with 1 and 4 mg/liter 2,4-D, respectively (Table 2). The incidence rate of non-regenerable type 4 calli was reduced 1.8–3.4 times by addition of 0.01 mg/liter BA in combination with 2,4-D. Therefore, 0.01 mg/liter BA in combination with 1 or 4 mg/liter 2,4-D were used for further growth of types 1–2 or 3 calli, respectively. Subculturings of types 2 and 3 calli resulted in the mixture of types 1, 2, 3 and 4 calli with a similar incidence rate to those with type 1 calli subculturing. However the subculturing of type 4 calli resulted in only type 4 calli. Interestingly, types 1–3 calli exhibited morphological variations when different hormonal combinations were used. Furthermore, when calli were subcultured in the light for 3 days before subculturing, green calli emerged, from which little albino plants were regenerated on the shoot induction medium (FIG. 2C). By suppressing the occurrence of type 4 calli and by selecting green calli at every subculturing step, the regenerability of green plants from the callus lines can be maintained without any harmful effects over 2 years (FIG. 2C).

The close relationship between callus morphology and shoot regenerability has been demonstrated in various plant species (Armstrong and Green 1985; Ke and Lee 1996; Luo and Jia 1998). In Kentucky bluegrass (*Poa pratensis* L.), calli induced from coleoptiles and embryos could be classified into four types based on the morphology and friability (Ke and Lee 1996). Type 4 calli of Kentucky bluegrass was soft, non-structured, and translucent, from which shoots were not regenerated at all. This result is similar to that obtained with zoysiagrass. Induction of type 4 calli in Kentucky bluegrass could be controlled only with auxin, while that of zoysiagrass could be controlled by decreasing the cytokinin level. In *Astrangalus adsurgens,* the hypocotyl-derived calli were also classified into four types (Luo and Jia 1998), but none of the four callus types showed morphological changes even after subculturing for 8 months. On the other hand, subculturing of each of the types 1–3 zoysiagrass callus types, but the type 4, resulted in four callus types. These differences among zoysiagrass, kentucky bluegrass, and *Astrangalus adsurgens* would reflect differential regenerabilities among different species.

Factors Affecting Transformation Efficiency

Effect of Callus Types

Types 1 and 2 calli proliferated on the MSCG1 medium and type 3 calli proliferated on the MSCG4 medium were co-cultivated with the *A. tumefaciens* EHA101 (pIG121Hm) for 6 days on 2,4-D-free co-cultivation media, and GUS expression measurement was employed to examine the relationship between different callus types and transformation efficiencies (Table 3, FIG. 2A).

Table 3 shows the transformation efficiencies of different callus types. Three Callus types were co-cultivated on the 2,4-D-free MSAS media (see Table 1) for 6 days in the dark at 26° C. Three replicates were measured and averaged.

TABLE 3

Effect of callus types on *A. tumefaciens*-mediated transformation of zoysiagrass

| Callus type | GUS blue spots/gram fresh weight |
|---|---|
| 1 | 21 ± 4 |
| 2 | 0 |
| 3 | 721 ± 201 |

GUS expression was detected on types 1 and 3 calli, but blue spots were not detected on type 2 calli. Type 3 calli gave the highest GUS expression frequency of 721±201 blue spots per 1 g fresh weight of calli, which was 34 times higher than that observed on type 1 calli. This result indicates that type 3 calli are more readily transformed than any other callus types.

Effect of 2,4-D Concentrations

Figure 3:
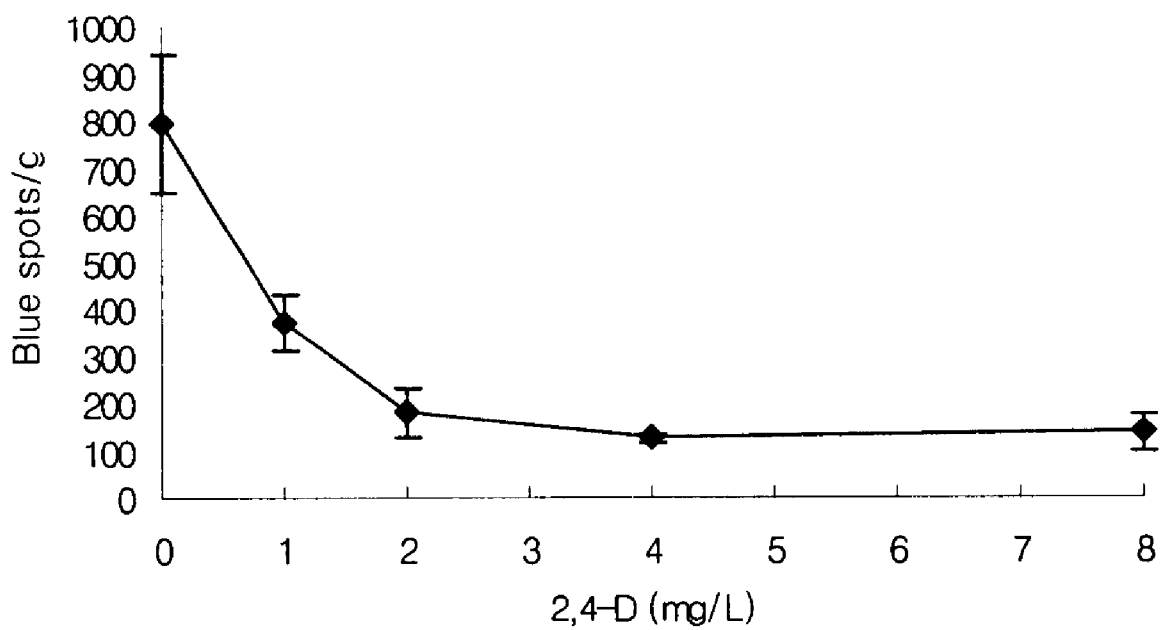
FIG. 3 shows 2,4-D effects on the transformation efficiency. Blue spots were counted per gram fresh weight calli cultured on a callus growth media containing different concentrations of 2,4-D.

Transformation frequency of each callus type, as judged by number of blue spots per unit fresh weight calli was also influenced by 2,4-D concentration in the co-cultivation media as shown in table 2. The effect of 2,4-D in the co-cultivation media was examined by counting blue spots on the calli proliferated on the MSCG4 medium (FIG. 3). After 9 days of co-cultivation, the blue spots were 793±145 per 1 g fresh weight of calli on the 2,4-D-free co-cultivation medium. However the number of blue spots decreased as the 2,4-D concentration increased (FIG. 3). This observation suggests that 2,4-D has a negative effect on the Agrobacterium-mediated transformation efficiency, which is contrary to those observed in other plants. A positive role for active cell division in the Agrobacteium-mediated transformation has been discussed in various plant species. In flax (McHughen et al. 1989) and eggplant (Claudia et al. 2000), pre-cultivation of explants on the regeneration medium containing 2,4-D before Agrobacterium-infection was necessary for efficient gene transfer. Active cell division in the injured explants greatly improved the integration of T-DNA fragment into plant genomic DNA (McHughen et al. 1989; Muthukumar et al. 1996; Claudia et al. 2000). It is possible that the 2,4-D-free co-cultivation media may activate cell division of zoysiagrass callus or promote the gene transfer itself, although the exact molecular mechanism is to be elucidated.

Co-cultivation Periods

Co-cultivation periods of 2–3 days has been generally used in the Gramineae transformations (Hiei et al. 1994; Rashid et al. 1996; Dong et al. 1996; Ishida et al. 1996, Cheng et al. 1997), while prolonged co-cultivation periods of up to 5–7 days has been shown to increase the Agrobacterium-mediated transformation efficiency in lilium usitatissimum, citrange, and agapanthus (Cervera et al. 1998; Suzuki et al. 2001). Prolonged co-cultivation period results in massive proliferation of the bacterial cells and usually decreases the regeneration frequency (Cervera et al. 1998). Although overgrowth of the bacterial cells was observed during the 6-day co-cultivation period, thorough washings by vortexing is able to prevent the calli from bacterial contamination, and the transformation frequency did not decrease (data not shown).

$CaCl_2$ Concentration in Co-cultivation Medium

Figure 4:
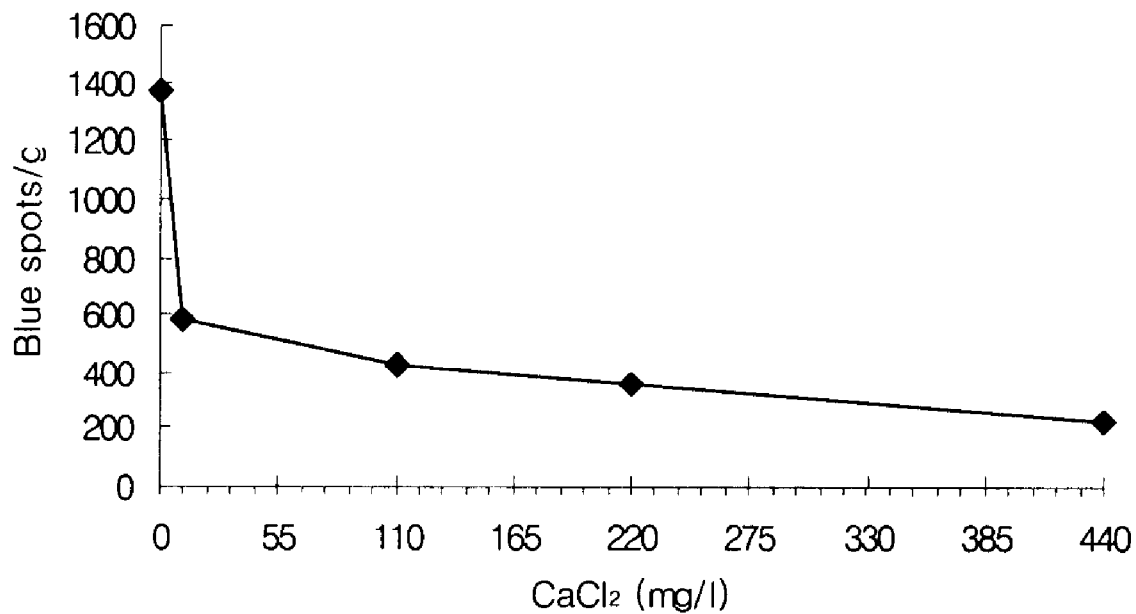
FIG. 4 shows effects of $CaCl_2$ on the transformation efficiency. A. tumefaciens-infected calli were cultured as described in FIG. 3, but the media contained different concentrations of $CaCl_2$.

Effect of $CaCl_2$ on the *A. tumefaciens*-mediated transformation frequency was investigated. Calcium-free co-cultivation medium significantly enhanced the number of GUS expressing blue spots (FIG. 4). The blue spots were 1368 per 1 g fresh weight calli on the $CaCl_2$-free co-cultivation medium but decreased as the $CaCl_2$ concentration increased. However, the callus growth was slower on the calcium-free co-cultivation medium than on the calcium-containing media. Therefore, calli must be immediately transferred to the calcium-containing callus growth medium after co-cultivation. A similar calcium effect has been observed with *Hevea brasuliensis* (Montoro et al. 2000).

Calcium plays a crucial role in plant responses to pathogenic infection and has been discussed in recent physiological studies (Dierk 1998). The calcium-mediated plant defence machinery may be also triggered in the zoysiagrass calli when infected with Agrobacterial cells. This may explain why zoysiagrass calli are more readily infected on the calcium-free co-cultivation medium.

Effect of Acetosyringone Concentrations

The phenolic compound acetosyringone is well known as an inducer that activates the vir gene expression in the Ti plasmid of Agrobacterium (Stachel et al. 1985). Acetosyringone has been shown to be critical for the Agrobacterium-mediated transformation in monocot plants, such as japonica and indica rice (Hiei et al. 1994; Rashid et al. 1996), pharaenopsis orchid, and agapanthus (Suzuki et al. 2001). It also greatly enhances the transformation efficiency in dicot plants, such as cucumber, broccoli, soybean, and citrange (Nishibayashi et al. 1996; Cervera et al. 1998; Santarem et al. 1998; Henzi et al. 2000).

Figure 5:
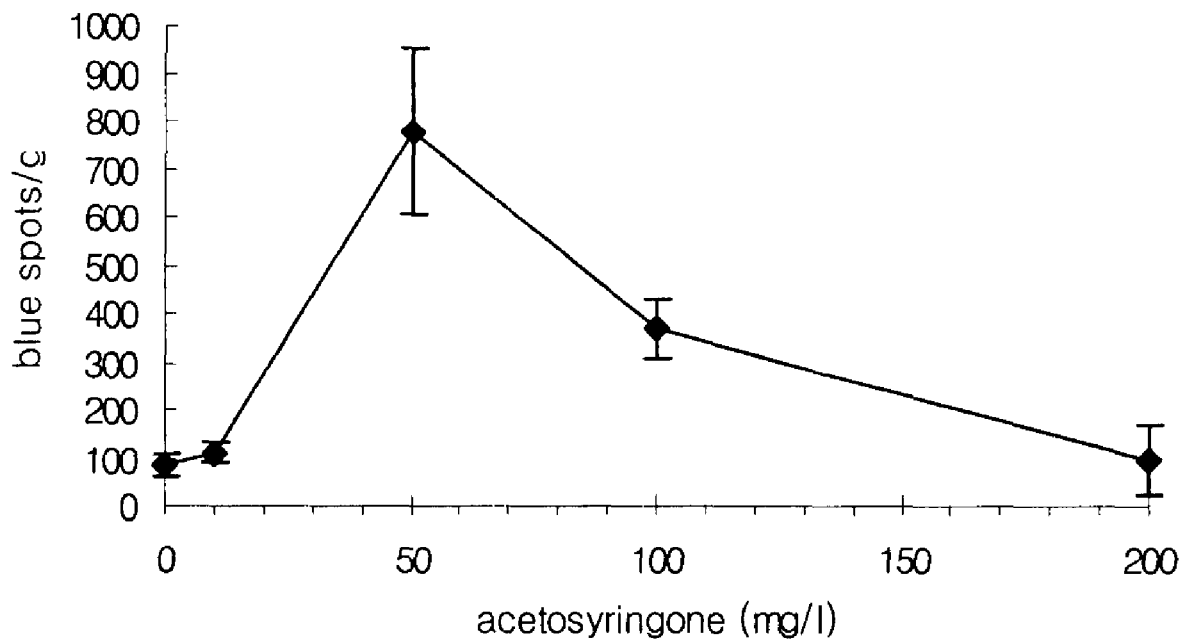
FIG. 5 shows effects of acetosyringone on the transformation efficiency. The experiments were carried out as describe in FIG. 3 but with various concentrations of acetosyringone.

When an acetosyringone-free co-cultivation medium was used, the transformation efficiency was very low with 86.3±24.0 blue spots per 1 g fresh weight calli. Addition of 50 mg/liter acetosyringone to the co-cultivation medium significantly increased by a factor of 9 the number of blue spots (FIG. 5). However, higher than 100 mg/liter concentrations had a negative effect on the transformation. Especially, the calli that co-cultivated on 200 mg/l acetosyringone-containing media did not grow on callus growth media after co-cultivation.

Transformation of Zoysiagrass with bar Gene

To evaluate the optimized transformation system for the zoysiagrass plant, the established protocol was applied to genetically transform the zoysiagrass plant with the pGPTV-HB transforming vector containing the herbicide-resistance gene (bar). Major components of the protocol were the use of type 3 calli and a co-culture period of 9 days. The co-cultivation media were free of 2,4-D and $CaCl_2$ but contained 50 mg/liter acetosyringone. The co-cultivated calli were propagated on the callus growth media and subject to shoot induction without hygromycin and bialaphos selection. Because Agrobacterial cell contamination was sometimes observed on the 125 mg/liter calbenicillin-containing media, 250 mg/liter of calbenicillin was used in the shoot induction media.

Selection was performed only on the rooting media containing 10 mg/liter hygromycin or 5 mg/liter bialaphos. Rooted shoots appeared after 4 weeks. When the rooted shoots were subcultured again on the fresh selection media for 2–4 weeks, escapes which rooted on the first selection media eventually died, while putative true transgenic plants rooted and elongated vigorously. The frequency of the resistant plants was about 20.5% (Table 4).

Table 4 shows survival rates of shoots regenerated from the *A. tumefaciens*-infected calli. Shoots regenerated from EHA101 (pGPTV-HB)-infected calli were cultured on the MSRS media (see Table 1) containing 5 mg/liter bialaphos (B) and 10 mg/liter hygromycin (H) for 4 weeks. The survival rates represent the number of produced resistant plants/shoots plated multiplied by 100.

TABLE 4

Survived Shoots from *A. tumefaciens*-Infected Calli.

| Experiments | Selection | Shoots plated | Produced resistant plants | Survival rate (%) |
|---|---|---|---|---|
| 1 | B | 36 | 2 | 5.6 |
| 2 | B | 57 | 0 | 0 |
| 3 | H | 44 | 9 | 20.4 |
| 4 | H | 62 | 6 | 9.7 |
| 5 | H | 38 | 3 | 7.9 |
| 6 | H | 54 | 0 | 0 |

Shoots regenerated from EHA101 (pGPTV-HB)-infected calli were cultured on the MSRS media containing 5 mg/liter bialaphos (B) or 10 mg/liter hygromycin (H) for 4 weeks. Survival rate = produced resistant plants/shoots plated × 100

Herbicide Resistance Assay on the Transgenic Zoysiagrass Plants

After transgenic and non-transgenic plants were established in soil, they were sprayed with 5 g/liter herbiace solution (Meiji Seika, Japan) every day for 2 weeks. After 2 weeks of herbicide application, transgenic plants survived bialaphos painting and grew to maturity. However the control plants stopped growing and eventually died (FIG. 3). The result demonstrates that the bar gene is normally expressed in the transgenic plants.

DNA Gel Blot Analysis

Figure 6:
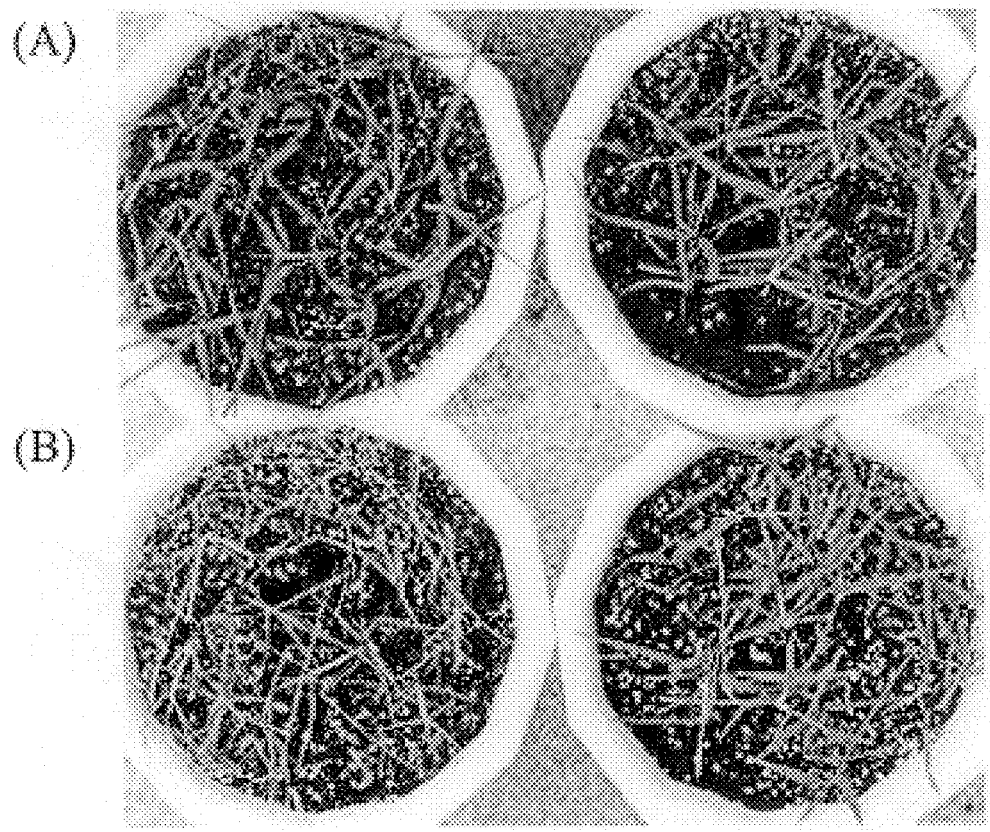
FIG. 6 shows transgenic (right) and parental (left) zoysiagrass plants. The zoysiagrass plants were splayed with herbicide solution every day for 2 weeks (5 gram/liter bilaphos).
Figure 7:
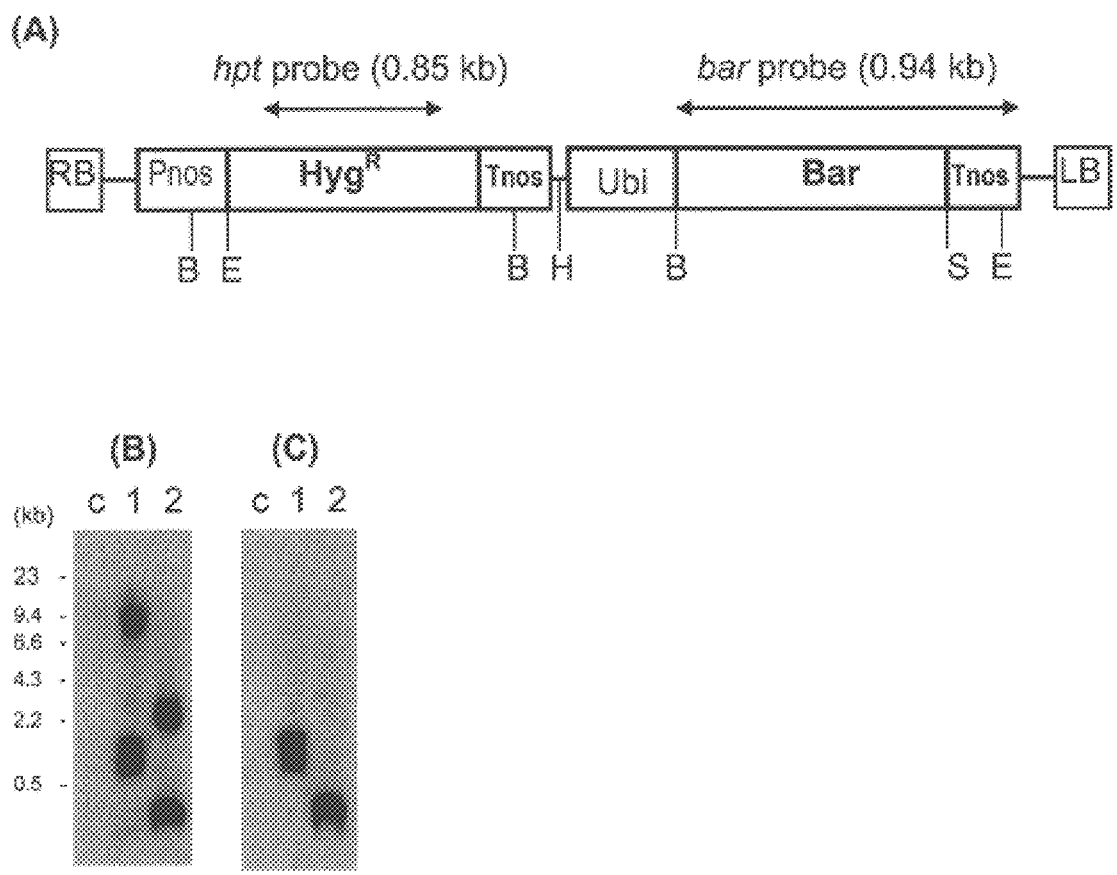
FIG. 7 shows a diagrammatic display of the transformation vector and Southern blot analyses to confirm the presence of the herbicide resistance (bar) gene in the plant genome.

To verify that the herbicide resistance of the transgenic zoysiagrass plant is derived from the bar gene integrated into the plant genome, the bialaphos-resistant plant was analyzed by DNA gel blot analysis. Genomic DNA was isolated from the transgenic plant, digested with HindIII, and allowed to hybridize with the bar- or hpt-specific probe (FIG. 6A). Concurrently, genomic DNA from control plants was also analyzed in an identical way. Control sample did not show any bands (FIG. 7B, lane c; FIG. 7C, lane c), while the samples from the transgenic plant showed bands specifically hybridised with the bar- and hpt-specific probe (FIG. 7B, lane 1; FIG. 7C, lane 1). Since the T-DNA fragment of the pGPTV-HB has a single HindIII site (FIG. 7A), the number of hybridized bands reflected the copy number of the integrated gene copies in the transgenic zoysiagrass plant. The detected bands represented fragments of larger than 1.6 or 1.8 kb for the bar- or hpt-specific probe, respectively, as expected from the map of the pGPTV-HB (FIG. 7A). This indicated that the copy number of the integrated gene was two (FIG. 7B, lane 1; FIG. 7C, lane 1). Genomic DNA Southern blot with BamHI and the bar probe also gave the same result, indicating that the copy number was two (FIG. 7B, lane 2). These results indicate that there were two stable integration events, clearly demonstrating that the observed herbicide resistance in the transgenic plant was determined by the integrated bar gene.

The *A. tumefaciens*-mediated transformation system for zoysiagrass in the present invention will speed up the genetic engineering of zoysiagrass as well as of closely related turfgrass species. The present invention provides optimized media compositions and culture conditions for a genetic transformation for zoysiagrass, which is valuable especially when a gene of interest is to be introduced into zoysiagrass with an aim to improve resistance to biotic and abiotic stress and to modulate the growth rate.

References

Armstrong C L, Green C E (1985) Establishment and maintenance of friable, embryogenic maize callus and the involvement of L-proline. Planta 164:207–214

Asano Y (1989) Somatic embryogenesis and protoplast culture in Japanese lawngrass (*Zoysia japonica*). Plant Cell Rep 8: 141–143

Bae C-H, Tohyama K, Lee S C, Lim Y P, Kim H I, Song P S, Lee H Y (2001) Efficient plant regeneration using mature seed-derived callus in Zoysiagrass (*Zoysia japonica* Steud.). Korean J Plant Tissue Cult 28:61–67

Cervera M, Pina J A, Juárez J, Navarro L, Peña L (1998) Agrobacterium-mediated transformation of citrange: Factors affecting transformation and regeneration. Plant Cell Rep 18:271–278

Chai B, Sticklen M B (1998) Applications of biotechnology in turfgrass genetic improvement. Crop Sci 38:1320–1338

Cheng M, Fry J E, Pang S, Zhou H, Hironaka C M, Duncan D R, Conner T W, Wan Y (1997) Genetic transformation of wheat mediated by *Agrobacterium tumefaciens*. Plant Physiol 115:971–980.

Claudia M, Ana P, Machado R, Marcia M-P, Gilberto S-M, Elisabeth M (2000) Establishment of an efficient Agrobacterium-mediated transformation system for eggplant and study of a potential biotechnologically useful promoter. J Plant Biotechnol 2:43–49

Dierk S (1998) Resistance response physiology and signal transduction. Curr Biol 1:305–310

Dong J, Teng W, Buchholz W G, Hall T C (1996) Agrobacterium-mediated transformation of Javanica rice. Mol Breeding 2:267–276

Henzi M X, Christey M C, McNeil D L (2000) Factors that influence *Agrobacterium rhizogenes*-mediated transformation of broccoli (*Brassica oleracea* L. var. italica). Plant Cell Rep 19:994–999

Hiei Y, Ohta S, Komari T, Kumashiro T (1994) Efficient transformation of rice (*Oryza sativa* L.) mediated by Agrobacterium and sequence analysis of the boundaries of the T-DNA. Plant J 6:271–282.

Inokuma C, Sugiura K, Imaizumi N, Cho C (1998) Transgenic Japanese lawngrass (*Zoysia japonica* Steud.) plants regenerated from protoplasts. Plant Cell Rep 17:334–338.

Ishida Y, Saito H, Ohta S, Hiei Y, Komari T, Kumashiro T. (1996) High efficiency transformation of maize (*Zea mays* L.) mediated by *Agrobacterium tumefaciens*. Nature Biotechnol 14:745–750.

Ke S, Lee C W (1996) Plant regeneration in Kentucky bluegrass (*Poa pratensis* L.) via coleoptile tissue cultures. Plant Cell Rep 15: 882–887

Luo J P, Jia J F (1998) Callus induction and plant regeneration from hypocotyl explants of the forage legume *Astragalus adsurgens*. Plant Cell Rep 17:567–570

McHughen A, Jordan M, Feist G (1989) A preculture period prior to Agrobacterium inoculation increase production of transgenic plants. J Plant Physiol 135:245–248

Montoro P, Teinseree, Rattana W, Kongsawadworakul, Michaux-Ferriere N (2000) Effect of exogenous calcium on *Agrobacterium tumefaciens*-mediated gene transfer in *Hevea brasiliensis* (rubber tree) friable calli. Plant Cell Rep 19:851–855

Muthukumar B, Mariamma M, Velulhambi K, Gnanam A (1996) Genetic transformation of cotyledon explants of cowpea (*Vigna unguiculata* L. Walp) using *Agrobacterium tumefaciens*. Plant Cell Rep 15:980–985

Nishibayashi S, Kaneko H, Hayakawa T (1996) Transformation of cucumber (*Cucumis sativus* L.) plants using *Agrobacterium tumefaciens* and regeneration from hypocotyl explants. Plant Cell Rep 15; 809–814

Park G H and Ahn B J (1998) Electroporation conditions for DNA transfer into somatic embryogenic cells of *Zoysia japonica*. (1998) Korean J Plant Tissue 25:13–19

Rashid H, Yokoi K, Toriyama K, Hinata, K. (1996) Transgenic plant production mediated by Agrobacterium in Indica rice. Plant Cell Rep 15:727–730.

Roger S O, Bendich A J (1985) Extraction of DNA from milligram amounts of fresh, herbarium and mummified plant tissues. Plant Mol Biol 5:69–76

Sambrook J, Fritsch E F, Maniatis T (1989) Molecular cloning. Cold Spring Harbor Lab Press, Cold Spring Harbor, N.Y.

Santarem E R, Trick H N, Essig J S, Finer J J (1998) Sonication-assisted Agrobacterium-mediated transformation of soybean immature cotyledons: optimization of transient expression. Plant Cell Rep 17:752–759

Schenk P M, Elliott A R, Manners J M (1998) Assessment of transient gene expression in plant tissues using the green fluorescent protein as a reference. Plant Mol Biol Rep 16:313–322

Southern E M (1975) Detection of specific sequences among DNA fragments separated by gel electrophoresis. J Mol Biol 98:503–517

Stachel S E, Messens E, Van Montagu M, Zambryski P (1985) Identification of the signal molecules produced by wounded plant cells that activate T-DNA transfer in *Agrobacterium tumefaciens*. Nature 318:624–629

Suzuki S, Supaibulwatana K, Mii M, Nakano M (2001) Production of transgenic plants of the Liliaceous ornamental plant *Agapanthus praecox* ssp. orientalis (Leighton) Leighton via Agrobacterium-mediated transformation of embryogenic calli. Plant Sci 161:89–97

Yu T T, Skinner D Z, Liang G H, Trick H N, Huang B, Muthukrishnan S (2000) Agrobacterium-mediated transformation of creeping bentgrass using GFP as a reporter gene. Hereditas 133:229–234

What is claimed is:

1. A method for producing a genetically transformed zoysiagrass comprising the steps of:

i) inducing and growing the calli obtained from seed of a zoysiagrass on MS medium containing 3% sucrose, 100 mg/L alpha-ketoglutaric acid, 4 mg/L thiamine-HCl, 2 mg/L 2,4-D, 0.2 mg/L BA, and 0.2% GELRITE;

ii) infecting the calli of the zoysiagrass with Agrobacterium cells to introduce a bialaphos resistance bar DNA coding sequence to the calli of zoysiagrass;

iii) co-cultivating the calli of the zoysiagrass and Agrobacterium cells in a co-cultivation medium containing acetosyringone and lacking both 2,4-dichlorophenoxyacetic acid and calcium;

iv) eliminating the Agrobacterium cells from the co-cultivation medium; and v) regenerating the calli into transgenic zoysiagrass.

2. A transgenic zoysiagrass produced by the method of claim 1, which is stably transformed with the bialaphos resistance bar DNA coding sequence.

3. The transgenic zoysiagrass of claim 2, which has been transformed with an ubiquitin promoter from maize, wherein said promoter is operably linked to said bialaphos resistance bar DNA coding sequence.

* * * * *